United States Patent [19]

Kurihara et al.

[11] Patent Number: 5,726,180
[45] Date of Patent: Mar. 10, 1998

[54] STABILIZED SOLID PHARMACEUTICAL PREPARATION AND METHOD OF PRODUCING THE SAME

[75] Inventors: Masahiko Kurihara, Ikeda; Shunichi Itoh, Suita; Kou Moriyama, Tokyo; Mitsutaka Isobe; Kenichiro Kiyoshima, both of Suita, all of Japan

[73] Assignee: Takeda Chemical Industries, Ltd., Osaka, Japan

[21] Appl. No.: 742,179

[22] Filed: Oct. 30, 1996

Related U.S. Application Data

[62] Division of Ser. No. 266,641, Jun. 28, 1994, Pat. No. 5,604,232.

[30] Foreign Application Priority Data

Jun. 30, 1993 [JP] Japan ................. 5-161158

[51] Int. Cl.$^6$ .......................... A01N 43/90; A61K 31/33
[52] U.S. Cl. .................. 514/264; 514/289; 514/568; 514/849
[58] Field of Search ............ 424/78.08; 514/264, 514/568

[56] References Cited

U.S. PATENT DOCUMENTS

| | | | |
|---|---|---|---|
| 4,049,803 | 9/1977 | Cotty et al. | 514/162 |
| 4,420,483 | 12/1983 | Sunshine et al. | 424/264 |
| 4,593,026 | 6/1986 | Guinot | 514/264 |

FOREIGN PATENT DOCUMENTS

| | | | |
|---|---|---|---|
| 0 566 393 | 10/1993 | European Pat. Off. | |
| 54-23132 | 2/1979 | Japan | 514/264 |
| 56-154416 | 11/1981 | Japan | 514/264 |
| WO85/045989 | 10/1985 | WIPO | |
| WO91/17746 | 11/1991 | WIPO | |

OTHER PUBLICATIONS

JP–67004062 Derwent Abstract 63:11–13.
Chemical Abstracts 109:156338 Yang et al.
Tan et al., Analytica Chimica Acta., vol. 226, No. 1, pp. 159–164 (1989).
Chugai Pharm. Co., Ltd. Database WP1, Week 6800 Derwent Pub. Ltd., GB AN67–08368g JP–B–42004062.

*Primary Examiner*—Peter F. Kulkosky
*Attorney, Agent, or Firm*—Wenderoth, Lind & Ponack

[57] ABSTRACT

To stabilize the active ingredients, a caffeine is incorporated into a solid pharmaceutical preparation comprising a dextromethorphan and a phenylpropanolamine. The pharmaceutical preparation may further comprise ibuprofen. The active ingredients may be further stabilized, in combination with the incorporation of the caffeine, by grouping and incorporating separately each or suitably combined plural of the active ingredients into different groups or by minimizing the amount of any reducing sugar such as lactose. The solid pharmaceutical preparation is practically valuable since decomposition of each active ingredient with the lapse of time is remarkably suppressed and the active ingredients are stabilized for a longer period of time.

16 Claims, No Drawings

STABILIZED SOLID PHARMACEUTICAL PREPARATION AND METHOD OF PRODUCING THE SAME

This application is a division of application Ser. No. 08/266,641 filed June 28, 1994 now U.S. Pat. No. 5,604,232.

FIELD OF THE INVENTION

The present invention relates to a stabilized solid pharmaceutical preparation which is useful for therapy and prophylaxis of various symptoms of cold, and a method of producing the same. In more detail, the present invention relates to a stabilized solid pharmaceutical preparation which comprises a dextromethorphan as an antitussive and/or an expectorant, a phenylpropanolamine as a decongestant effective for nasal mucus and nasal congestion, and a caffeine, and which may further comprise ibuprofen as an antipuretic, analgesic and/or antiinflammatory agent, and method of producing such preparations. Particularly, the present invention provides a stabilized pharmaceutical preparation comprising a dextromethorphan, ibuprofen and a phenylpropanolamine which are stabilized by further adding a caffeine to suppress or inhibit decomposition of each of the active ingredients even when these active ingredients are incorporated or granulated in one group.

BACKGROUND OF THE INVENTION

Ibuprofen was first synthesized by Nicholson and Adamo in 1964, developed as a drug by Boots Pure Drug Co., Ltd., England, and has been utilized mainly as an antipyretic, analgesic and/or antiinflammatory agent. A phenylpropanolamine is a sympathomimetic drug having ephedrine-like pharmacological activities and therapeutic activities for nasal mucus and nasal congestion, and utilized as a drug for rhinitis in nonproprietary drugs.

In JP-A-61-501913 corresponding to WO85/04589, and in WO91/17746, there are disclosed, for instance, pharmaceutical compositions of cold remedies comprising a non-steroidal antiinflammatory agent such as ibuprofen and the like as an analgesic ingredient, phenylpropanolamine hydrochloride as a decongestive ingredient, dextromethorphan hydrobromide as an antitussive and chlorpheniramine maleate as an antihistamine. These pharmaceutical preparations are prepared by mixing dextromethorphan, ibuprofen and phenylpropanolamine hydrochloride directly with lactose and/or other base without being subjected to stabilization.

As a result of various investigations for preparing general cold remedies having more excellent actions, the present inventors found that pharmaceutical preparations comprising the dextromethorphan, the phenylpropanolamine (e.g. phenylpropanolamine hydrochloride, etc.) and further comprising ibuprofen are particularly favorable as cold remedies.

These pharmaceutical preparations, however, deteriorate or impair the stability of the active ingredients, and, thus, cause not only decrease of the effective amounts of the ingredients but also change of the external appearance with the lapse of time.

More precisely, it is confirmed that decomposition of phenylpropanolamine hydrochloride occurs by the reaction with some kinds of sugars, and by pH variation of a solution [R. H. Barry., J. Pharm. Sci., 71, No.1, January 116–118, (1982)]. "Researches for incompatibility of pharmaceutical preparations" [Ueda, Report of Pharmacological Research Institute of Toyama Pref., Vol. 1984/1985, p127–234, (1987)] discloses that phenylpropanolamine hydrochloride is incompatible with lysozyme chloride, potassium guaiacolsulfonate, dextromethorphan hydrobromide and so on.

On the other hand, since ibuprofen has a lower melting point of 75° C., when ibuprofen is coexisted with other ingredients, it may frequently cause melting point depression of the other ingredients. Further, a pharmaceutical composition comprising ibuprofen and other ingredient has low drug stability, thus it is liable to cause inactivation of active ingredients, change of external appearance and so on. For instance, "Incompatibility of ibuprofen granules" [Sato, Pharmacy, 27, 12, 73–78, (1976)] discloses that ibuprofen is incompatible with methylephedrine or sodium bicarbonate, and "Researches for incompatibility of pharmaceutical preparations" [Ueda, Report of Pharmacological Research Institute of Toyama Pref., Vol. 1984/1985, p127–234, (1987)] discloses that ibuprofen is incompatible with dl-chlorpheniramine maleate, ascorbic acid and so on.

Such problems as described above are particularly remarkable in a pharmaceutical preparation comprising a phenylpropanolamine, a dextromethorphan and ibuprofen. For example, in a pharmaceutical preparation containing dextromethorphan hydrobromide, ibuprofen and phenylpropanolamine hydrochloride as described in undermentioned Experimental Example 1, each of the ingredients is liable to be decomposed at a high temperature with the passage of time. Particularly, the stability of phenylpropanolamine hydrochloride is impaired and change of the external appearance occurs with incorporation of ibuprofen and dextromethorphan hydrobromide. Therefore, among pharmaceutical preparations comprising a dextromethorphan, ibuprofen, a phenylpropanolamine and the like, no successfully stabilized pharmaceutical preparation having adequate utility has been developed yet.

SUMMARY OF THE INVENTION

Accordingly, it is an object of the present invention to provide a solid pharmaceutical preparation in which even though a dextromethorphan and a phenylpropanolamine being incompatible with each other are contained as active ingredients, these active ingredients are stabilized therein, and a method of producing such a solid pharmaceutical preparation.

It is another object of the invention to provide a solid pharmaceutical preparation in which ibuprofen is further contained in addition to the ingredients of a dextromethorphan and a phenylpropanolamine, and each of these active ingredients is stabilized, and a method of producing the same.

It is still another object of the present invention to provide a solid pharmaceutical preparation in which inactivity of a dextromethorphan and a phenylpropanolamine, and further of ibuprofen and change of the external appearance of the pharmaceutical preparation with the passage of time are remarkably suppressed, and thus a longer quality assurance period and a higher quality of products are obtained, and to provide a method of producing such a pharmaceutical preparation.

It is a further object of the invention to provide a method for efficiently stabilizing a dextromethorphan and a phenylpropanolamine being incompatible with each other, and still more incompatible with ibuprofen.

A still further object of the present invention is to provide a method for stabilizing the active ingredients, especially the phenylpropanolamine while maintaining high level stability for a longer duration of time.

Another object of the invention is to provide a solid pharmaceutical preparation useful for a cold remedy such as a general or complex cold remedy and the like, and to provide a method of producing such a preparation.

As a result of intensive investigations for stabilization of a pharmaceutical preparation comprising a dextromethorphan, ibuprofen and a phenylpropanolamine, the inventors of the present invention found that incorporation of a caffeine into the dextromethorphan, the phenylpropanolamine and, if necessary, ibuprofen unexpectedly increases or improves the stability of these ingredients remarkably, and that separated incorporation of the phenylpropanolamine group further increases the stability of the active ingredients and a stabilized pharmaceutical preparation is thus obtained. The present invention has been accomplished based on these findings and further researches.

Accordingly, the present invention provides (A) a stabilized solid pharmaceutical preparation comprising a dextromethorphan, a phenylpropanolamine and a caffeine, and these ingredients being stabilized, and (B) the stabilized solid pharmaceutical preparation which further comprises ibuprofen. In these pharmaceutical preparations, the dextromethorphan and the phenylpropanolamine (for instance, phenylpropanolamine hydrochloride, etc.) may be incorporated into different groups respectively, and ibuprofen may be compounded into the group of the dextromethorphan. Furthermore, in the phenylpropanolamine group, the content of a reducing sugar may be minimized or controlled to such an amount as to adversely affect the drug stability.

According to the method of the present invention, a caffeine is incorporated into a solid pharmaceutical preparation comprising a dextromethorphan, a phenylpropanolamine, and if necessary, ibuprofen as active ingredients to stabilize these active ingredients. In the stabilizing method, the morphology of the caffeine in the preparation is not particularly restricted, and the stabilization of each active ingredient can be realized as far as the caffeine is coexistent in or with the solid pharmaceutical preparation.

Further, in accordance with the method of the present invention, a stabilized solid pharmaceutical preparation is produced by incorporating a caffeine into a solid pharmaceutical preparation comprising a dextromethorphan and a phenylpropanolamine. In this method, (i) a granulated preparation containing at least one active ingredient selected from the dextromethorphan, the phenylpropanolamine, the caffeine and, if any, ibuprofen, and (ii) an optionally granulated other active ingredient(s) may be mixed. The plural active ingredients may individually be granulated to form a number of granulated preparations corresponding to each of the active ingredients, or may form one or more of granulated preparations wherein two or more of the active ingredients are contained in one granulated preparation.

In this specification, the term "incorporating into different groups" refers to any and all cases in which, for example, the dextromethorphan group and the phenylpropanolamine group are contained in the form wherein the contact with each other is inhibited or suppressed. The term "incorporating into different groups" may hereinafter be referred to as "grouping and incorporating separately". The term "phenylpropanolamine group" means a group containing the phenylpropanolamine. The term "granulated preparation" includes common products or preparations granulated by any means as well as fine granules, granules and pills.

Typical examples of the solid pharmaceutical preparation of the present invention include solid pharmaceutical preparations for oral administration such as granulated preparations (for instance, fine granules, granules, pills and others), tablets, capsules and so on. The pharmaceutical preparation of the invention is suitable for a cold remedy among others.

DETAILED DESCRIPTION OF THE INVENTION

The dextromethorphan used in the invention includes dextromethorphan (dextromethorphane) and salts thereof, for example, dextromethorphan hydrobromide, dextromethorphan.phenolphthalate and so on. The phenylpropanolamine contained as another active ingredient in the solid pharmaceutical preparation of the invention includes any pharmacologically acceptable salts and may be, for example, phenylpropanolamine hydrochloride and others.

Examples of the caffeine include caffeine and derivatives therefrom such as caffeine anhydride, caffeine monohydrate, caffeine citrate, caffeine sodium benzoate and the like.

The pharmaceutical preparation of the present invention may contain, if desired, other active ingredients than the dextromethorphan, ibuprofen, the phenylpropanolamine and the caffeine. These active ingredients include, for example, antipyretic, analgesic and/or antiinflammatory agents, antitussive and/or expectorants, bronchodilators, Chinese medicine extracts, vitamins, gastric antacids and mucosa-protecting agents, minerals, amino acids and so on.

As the antipyretic, analgesic and/or antiinflammatory agents, there may be mentioned, for example, acetaminophen, phenacetin, aspirin, aspirin aluminium, ethenzamide, aminopyrine, salicylamide, lactylphenetidin, isopropylantipyrine, sasapyrine, sodium salicylate, phenylbutazone, ketophenylbutazone, indomethacin, naproxen, ibufenac, serratiopeptidase, lysozyme chloride, mefenamic acid, alkaloids of belladonna extract and so on.

Examples of the antitussive and/or expectorants include chloperastine hydrochloride, codeines such as dihydrocodeine phosphate and codeine phosphate, oxymetebanol, eprazinone hydrochloride, tipepidine, tipepidine citrate, ephedrine hydrochloride, alloclamide hydrochloride, carbetapentane phenate, dibunate sodium, tipepidine hibenzate, chloperastine phendizoate, trimetoquinol hydrochloride, methoxyphenamine hydrochloride, dl-methylephedrine hydrochloride, noscapine, noscapine hydrochloride, dimemorfan or a salt thereof (e.g. dimemorfan phosphate, dimemorfan sulfate, etc.), bromhexine hydrochloride and so on.

The bronchodilators include, for example, ephedrine, theophylline, diphenhydramine or a salt thereof (e.g. diphenhydramine hydrochloride, etc.), chlorpheniramine or a salt thereof (e.g. chlorpheniramine D-maleate, etc.) and so on.

Examples of the Chinese medicine extract include an extract from *Glycyrrhizae radix, Polygala senega, Bupleuri radix, Cinnamomi cortex, Pherariae radix, Ephedrae herba, Schizonepetae herba, Forsythiae fructus, Armeniacae semen, Pinellae tuber, Paeoniae radix, Asiasri radix, Zingiberis rhizoma* (ginger), *Schisandrae fructus, Perillae herba, Ginseng radix, Aurantii nobills pericarpium* and the like.

As examples of vitamins, there may be mentioned vitamin $B_1$, fursultiamine, vitamin $B_2$, vitamin C and so on. Gastric antacids and mucosa-protecting agents include, for instance, magnesium hydroxide, magnesium oxide, aluminium hydroxide, aluminium sulfate, magnesium metasilicate aluminate [e.g. Neusilin (Trade name)], magnesium silicate aluminate, synthetic hydrotalcite [e.g. ALCAMAC (Trade name)], coprecipitate of aluminium hydroxide and sodium bicarbonate [e.g. Kumulite (Trade name)], sucralfate and the like.

Where the pharmaceutical preparations of the present invention are utilized as cold remedies, these active ingredients are mixed usually in accordance with a standard for a cold remedy described in Drug Manufacturing Standard (revised in 1991, Yakugyo Jibosha Co., Ltd., Japan).

As described above, since the dextromethorphan is chemically incompatible with the phenylpropanolamine, a combinational use of both ingredients lowers or decreases the stability of each of the active ingredients. Further, use of ibuprofen in combination with the ingredients also tends to lower or decrease the stability of each active ingredients. Such combinations of the active ingredients particularly impairs the stability of the phenylpropanolamine. For stabilization of such active ingredients being incompatible with each other, the caffeine is effectively and advantageously used.

In this invention, depending on the content, caffeine may exhibit pharmaceutical activities in addition to a stabilizing effect for the other active ingredients.

In the pharmaceutical preparation (A) in which the caffeine is incorporated with the dextromethorphan and the phenylpropanolamine as active ingredients and ibuprofen is not contained, the effective amount of the caffeine so as to sufficiently stabilize the active ingredients is, about 2 to 1,000 parts by weight, preferably about 4 to 750 parts by weight, and more preferably about 7 to 500 parts by weight relative to 100 parts by weight of the total weight of the two active ingredients. Particularly preferred amount of the caffeine is about 10 to 300 parts by weight, preferably about 15 to 200 parts by weight and more preferably about 25 to 100 parts by weight relative to 100 parts by weight of the total weight of the active ingredients.

The content of each active ingredient in the pharmaceutical preparation (A) may be selected from a suitable range. The pharmaceutical preparation usually comprises the dextromethorphan in a proportion of about 1 to 25% by weight and preferably about 2 to 20% by weight; the phenylpropanolamine in a proportion of about 2 to 35% by weight and preferably about 5 to 30% by weight; and the caffeine in a proportion of about 1 to 60% by weight, preferably about 2 to 55% by weight, and more preferably about 4 to 50% by weight, based on the total weight of the pharmaceutical preparation, and such preparation is economical and effective.

For improving or enhancing the stability of the active ingredients in the preparation (B) which comprises the caffeine in addition to the dextromethorphan, ibuprofen and the phenylpropanolamine as the active ingredients, the caffeine may preferably be contained in an amount of about 1 to 1,000 parts by weight, preferably about 3 to 750 parts by weight and more preferably about 5 to 500 parts by weight relative to 100 parts by weight of the total weight of the active ingredients. A typically preferred proportion of the caffeine is about 5 to 200 parts by weight, preferably about 10 to 100 parts by weight and more preferably about 12 to 50 parts by weight relative to 100 parts by weight of the total weight of the active ingredients.

The content of each of the active ingredients in the pharmaceutical preparation (B) can also be selected from a suitable range. An economical and effective amount is based on the total weight of the pharmaceutical preparation, about 1 to 15% by weight and preferably about 2 to 10% by weight of the dextromethorphan; about 1 to 20% by weight and preferably about 2 to 15% by weight of the phenylpropanolamine; about 5 to 70% by weight, and preferably about 10 to 60% by weight of ibuprofen; and about 1 to 80% by weight, preferably about 2 to 55% by weight and more preferably about 4 to 50% by weight of the caffeine.

In the pharmaceutical preparations (A) and (B), the amount of the caffeine relative to each of the active ingredients can be selected from the range depending on the species of the active ingredients, and is, for example, about 0.5 to 1,000 parts by weight, preferably about 5 to 500 parts by weight, more preferably about 10 to 300 parts by weight and practically about 25 to 200 parts by weight relative to 100 parts by weight of each of the active ingredients.

The present invention is characterized in that even though the dextromethorphan and ibuprofen are incompatible with the phenylpropanolamine, the stability of these active ingredients can be increased or improved by the caffeine. Therefore, the ingredients, can be incorporated into the same one group, and thus an improved producibility can be obtained. That is, even when (a) the phenylpropanolamine, and (b) ibuprofen and the dextromethorphan each chemically incompatible with the phenylpropanolamine are incorporated or compounded into the same group, decrease of the stability of the active ingredients can be greatly suppressed or inhibited by means of incorporation of the caffeine into the group, or coexistence of the caffeine with the group.

The pharmaceutical preparation in which the active ingredients are stabilized may also be obtained by (1) mixing a group containing the dextromethorphan and the phenylpropanolamine, and a group which is segregated from the former and contains the caffeine, or (2) mixing a group containing the dextromethorphan, ibuprofen and the phenylpropanolamine, and a group which is separated from the former and contains the caffeine.

Further, segregation of the dextromethorphan group from the phenylpropanolamine group into different groups is preferable for improving the stability of the active ingredients. Ibuprofen may frequently be contained in the dextromethorphan group. In this embodiment, for instance, (3) a method of separating or segregating each ingredient of the dextromethorphan, ibuprofen and the phenylpropanolamine from each other into different or separate groups, (4) a method of separating or segregating (a) the dextromethorphan group or a group containing the dextromethorphan and ibuprofen, from (b) the phenylpropanolamine group, or other methods can be employed. In these embodiments, the caffeine may be incorporated or contained in any group containing the active ingredient, for example, the phenylpropanolamine group, or may form a group being independent of another group containing the active ingredient.

The stabilizing effects of the present invention can be achieved by addition of the caffeine to a pharmaceutical preparation comprising the dextromethorphan, the phenylpropanolamine and, when necessary, ibuprofen.

In the manufacture of the preparation, ingredients having low compatibility with each other may respectively be incorporated or contained in different groups. Usually, a carrier can advantageously be used for suppressing or inhibiting the contact of the ingredients having low compatibility with each other.

As the carriers, unless contrary to the objects of the invention and harm to the stability of the active ingredients, various conventional additives used in the manufacture of granulated preparations may be employed. The carriers include various excipients such as lactose, sucrose, mannitol, corn starch, talc, crystalline cellulose [e.g. Avicel (Trade name) etc.], magnesium stearate, light silicic anhydride, magnesium carbonate, calcium carbonate, L-cysteine and the like; binders such as starch, alpha-starch, gelatin, powdered gum arabic, methylcellulose, carboxymethylcellulose, carboxymethylcellulose sodium, hydroxypropylcellulose, hydroxypropylmethylcellulose, polyvinylpyrrolidone, pullulan, dextrin and so on; disintegrators such as carboxymethylcellulose calcium [carmellose calcium, e.g. ECG 505 (Trade name)], a low-substituted hydroxypropylcellulose, croscarmellose sodium [for example, Acdisol (Trade name)], etc.; surfactants including anionic surfactants such as sodium alkylsulfates, and non-ionic surfactants such as polyoxyethylene-sorbitan fatty acid esters, polyoxyethylene-fatty acid esters and polyoxyethylene-castor oil derivatives; colorants; corrigents; adsorbents; preservatives; wetting agents; antistatic agents; disintegration retarders; and so on.

Among these carriers, at least an excipient and a binder are practically utilized, as well as a disintegrator.

As described above, in the pharmaceutical preparation of the invention, each ingredient of the dextromethorphan, ibuprofen and the phenylpropanolamine can be stabilized by incorporation of the caffeine.

In the preferred embodiments for the stabilization, at least one ingredient selected from the dextromethorphan (if desired with ibuprofen) and the phenylpropanolamine is contained in a granulated preparation which is granulated with a carrier. In this case, the ungranulated group of the active ingredient may be mixed with the granulated preparation containing the other active ingredient and the carrier.

Typically preferred embodiments include a solid pharmaceutical preparation in which the dextromethorphan, ibuprofen and the phenylpropanolamine are respectively grouped and segregated into different or separate granulated preparations. Such preferred pharmaceutical preparation may be obtained by granulating (a) the dextromethorphan and ibuprofen in the same group and (b) the phenylpropanolamine in the other group into granulated preparations respectively. The caffeine may be added to each group or to any one of the groups. Further, the caffeine may form a granulated preparation of an independent group separated from the granulated reparation(s) containing the active ingredient(s), so far as being coexistent with the groups of the active ingredients. In such case, the solid pharmaceutical preparation can be obtained by mixing granulated preparations prepared by grouping and incorporating separately, for instance, a granulated preparation of the dextromethorphan group, a granulated preparation of the ibuprofen group, and a granulated preparation of the phenylpropanolamine group.

Preferred methods for "grouping and incorporating separately", that is, for incorporating into different or separate groups, include, other than (1) the above-mentioned process which comprises granulating the active ingredients separately in different granulated preparations, and mixing the preparations so as to lessen the contact area of the active ingredients, (2) a process of filling capsules with a mixture of granulated preparations grouped and incorporated separately, (3) a process of molding a mixture of granulated preparations grouped and incorporated separately into tablets, (4) a process of molding granulated preparations grouped and incorporated separately into tablets having two or more layers using a multi-layer tablet machine (for example, a machine manufactured by Kikusui Seisakusho Co., Ltd., etc.), in which each different adjacent layer contains a different group, (5) a process of molding granulated preparations grouped and incorporated separately into sandwich-type tablets having multiple layers, in which a buffering layer (for instance a thin layer) is interposed between adjacent layers and (6) a process of coating or encapsulating at least one group of the active ingredients with a polymer to stabilize the active ingredients by separation or segregation.

As practically preferred embodiments of such methods, there may be mentioned the following processes.

For "grouping and incorporating separately", the dextromethorphan group may be prepared by a process which comprises mixing the dextromethorphan, and if necessary, other drug(s), and a carrier, preferably at least a binder and an excipient, and granulating the mixture in accordance with a conventional manner. When wet fluidized-bed granulation is employed, for example, the granulated preparation of the dextromethorphan group may be produced by mixing and charging suitable amount of additives such as an excipient, a disintegrator and the like, the dextromethorphan, and if desired, other drug(s), into a fluidized-bed granulator, spraying a binder such as an aqueous solution of hydroxypropylcellulose and the like into the granulator, and drying the granulation product to give a granulated preparation. Alternatively, a process which comprises extruding a kneaded product obtainable by stirring, kneading or the like, rounding or shaping the extruded product into spherical form or structure with the use of a rounding means such as a Marumerizer and drying the product.

The phenylpropanolamine group can also be obtained by the same granulation procedures as in the dextromethorphan group except for using the phenylpropanolamine instead of the dextromethorphan.

In any cases where the active ingredients are grouped and incorporated separately, or where those are compounded into the same group, when the phenylpropanolamine group contains a large quantity of a reducing sugar such as lactose, sucrose and the like, the stability of the phenylpropanolamine is impaired. Therefore, preferably, the amount of any reducing sugar contained in the phenylpropanolamine group is minimized to such an extent as to maintain the stability of the phenylpropanolamine. That is, the phenylpropanolamine group which does not contain a reducing sugar in such an amount as to harm or affect adversely the stability is preferable. Typical examples include (1) the phenylpropanolamine group which does not contain a reducing sugar, (2) even if containing a reducing sugar, the reducing sugar in the phenylpropanolamine group should be contained in a proportion of 10% by weight or less and preferably 7% by weight or less relative to the total weight of granulated preparation of the phenylpropanolamine group, and (3) the phenylpropanolamine group which contains a sugar alcohol which does not have a reducing hydroxyl group, such as mannitol, maltitol and sorbitol instead of a reducing sugar.

The stability of the phenylpropanolamine can be improved by the coexistent caffeine even when a reducing sugar is used with the phenylpropanolamine, and in some cases, with the dextromethorphan and/or ibuprofen which are incompatible with the phenylpropanolamine.

In the pharmaceutical preparation comprising ibuprofen, ibuprofen may be compounded into the dextromethorphan group, or may be granulated in a similar manner as in the dextromethorphan group to form a different or separate group. The caffeine grouped and incorporated separately may (a) be incorporated, with the active ingredient, into each group to be granulated, (b) be compounded into any one group to be granulated, or (c) be granulated as a separate group in the same processes as above.

The pharmaceutical preparation comprising the active ingredients incorporated into the same group may also be granulated in a conventional manner using the active ingredients and a carrier.

The granulation for producing the granulated preparation may be carried out by use of a conventional granulation method. As examples of such methods, there may be mentioned a wet granulation such as spray granulation, stirring granulation, fluidizing granulation, tumbling granulation and tumbling-fluidizing granulation or a dry granulation such as compacting granulation using a powdery or granular binder.

The solid pharmaceutical preparation according to the present invention may be provided in a variety of dosage forms such as fine granules, granules, pills, tablets obtainable by compression-molding the fine granules or granules, and capsules obtainable by filling capsules with the fine granules or granules. The mean particle size or diameter of the fine granules may be, for example, about 10 to 500 μm, preferably about 100 to 500 μm. The mean particle size or diameter of the granules may be, for example, about 500 to 1,500 μm.

The solid pharmaceutical preparations comprising a fine granule, a granule or a pill can be produced by (a) filling divided packages with a granulated preparation containing all active ingredients in the same group, or (b), in case of "grouping and incorporating separately" the active ingredients, blending granulated preparations containing one or more of the active ingredients (for instance, a granulated preparation of the dextromethorphan group which may further contain ibuprofen, a granulated preparation of the phenylpropanolamine group and, if desired, a granulated preparation of ibuprofen group), and filling divided packages with the mixture.

Capsules can be produced by means of filling directly, using a capsule-filling machine, capsules (c) with a granulated preparation containing all active ingredients in the same group or (d) with a mixture of granulated preparations containing one or more of the active ingredients (e.g. a granulated preparation of the dextromethorphan group which may further contain ibuprofen, a granulated preparation of the phenylpropanolamine group and, if necessary, a granulated preparation of the ibuprofen group) as well as by means of filling capsules with at least two of granulated preparations in the form of two or more layers where each adjacent layer contains a different granulated preparation respectively.

Tablets can be prepared by means of blending a granulated preparation containing the active ingredients in the same group, or granulated preparations containing one or more of the active ingredients (for example, a granulated preparation of the dextromethorphan group which may further contain ibuprofen, a granulated preparation of the phenylpropanolamine group and, if desired, a granulated preparation of the ibuprofen group), and a carrier (for instance, an excipient, a binder, a disintegrator and the like), and compressing and molding the mixture into a tablet.

Where the pharmaceutical preparation of the present invention is used as a cold remedy, the content of ibuprofen may be about 50 to 90% by weight and preferably about 60 to 80% by weight of the pharmaceutically commonly used amount of ibuprofen which is contained alone as an active ingredient. The proportion of the ibuprofen group depends on the type of the preparation, and may be, as the dose of ibuprofen for an adult, about 1 to 1,000 mg/day, preferably about 1 to 600 mg/day, and more preferably about 30 to 500 mg/day. The preparation contains the other ingredients, as the dose per day for an adult, the dextromethorphan group in such a proportion of about 1 to 100 mg, and preferably about 3 to 75 mg; the phenylpropanolamine as phenylpropanolamine hydrochloride in an amount of about 0.5 to 200 mg, and preferably about 1 to 100 mg; the caffeine in a proportion of about 3 to 500 mg, and preferably about 10 to 350 mg. The size of the pharmaceutical preparation selected depends on the amounts of the ingredients.

The pharmaceutical preparation of the present invention may be coated with a coating composition according to various objects. As the coating composition, a composition such as a sugar coating composition comprising a sugar as a main component, and a film formable composition comprising a cellulosic base as a main component may be employed.

Components for such coating compositions include, for example, sugars such as granulated sugar and mannitol, gum arabic, talc, hydroxypropylcellulose, hydroxypropylmethylcellulose, ethylcellulose, hydroxymethylcellulose, cellulose acetate phthalate, hydroxypropylmethylcellulose phthalate, hydroxymethylcellulose acetate succinate, an acrylic acid copolymer, carboxymethylethylcellulose, polyvinyl acetal diethylaminoacetate, shellac, waxes and so on. These components may be used in combination.

The coating composition may contain a conventional coating auxiliary. As such coating auxiliaries, there may be mentioned, for example, sugars such as lactose and mannitol, polyethylene glycol, polysorbate (e.g. Tween 80, etc.), colorants such as titanium oxide, red iron oxide and so on.

The coating amount of the coating composition can be selected according to the type or species of the solid pharmaceutical preparation, and is, relative to the solid pharmaceutical preparation, about 0.1 to 30% by weight, and preferably about 0.5 to 10% by weight for tablets, about 0.1 to 50% by weight, and preferably about 1 to 20% by weight for pills and granules, and about 0.1 to 100% by weight, and preferably about 1 to 50% by weight for fine granules.

Coating can be carried out by a conventional manner such as pan coating, air-suspension or fluidized bed coating, tumbling coating or centrifugal coating, or a combination of these procedures. When the coating composition is a solution or a dispersion containing water or an organic solvent, spray-coating can also be employed. The proportion of such water or organic solvent may for example be about 25 to 99% by weight. The type of organic solvent is not so critical, and includes, for example, alcohols such as methanol, ethanol, isopropyl alcohol, etc.; ketones such as acetone etc.; and halogenated hydrocarbons such as chloroform, dichloromethane, trichloroethane and the like. Typically preferred examples of the solvent include water and/or an alcohol, and specifically preferred is water.

Thus the solid pharmaceutical preparation of the present invention is stabilized wherein decomposition of the active ingredients with the passage of time is suppressed. When the solid pharmaceutical preparation of the present invention is used for the therapy of cold as a common cold remedy including a general or complex cold remedy for mammals such as human beings, the solid pharmaceutical preparation such as a tablet, a granule and a capsule and the like may be administered orally by a conventional manner.

The following examples, comparative examples and experimental examples are merely intended to illustrate the present invention in further detail and should not be construed as defining the scope of the invention.

EXAMPLES

Example 1

A high-shear type granulator (Vertical Granulator, FM-G25, manufactured by Powrex Corporation, Japan) was charged with 1,350 g of ibuprofen (hereinafter may be referred to as IBU), 144 g of dextromethorphan hydrobromide (hereinafter may be abbreviated as DMP), 225 g of phenylpropanolamine hydrochloride (hereinafter may be referred to as PPA), 225 g of caffeine anhydride (hereinafter may be abbreviated as CAF), 156 g of lactose, 600 g of crystalline cellulose, 150 g of hydroxypropylcellulose (may be abbreviated as HPC-L, hereinbelow) and 150 g of a low-substituted hydroxypropylcellulose (hereinafter may be referred to as L-HPC). The charged material was granulated with stirring by adding 1,200 g of purified water to give granulated product.

The granulated product was extrusion-molding into fine cylindrical or columnar form using an extrusion granulator (Domegran, DG-L1, manufactured by Fuji Paudal Co., Ltd., Japan) equipped with a punching screen of 0.35 mm φ, and rounded into spherical fine granules with use of Marumerizer (QJ-230, manufactured by Fuji Paudal Co., Ltd., Japan). The resultant spherical fine granules were dried at 40° C. in vacuo for 10 hours to give 2,750 g of fine granules.

Example 2

The high-shear type granulator was charged with 1,125 g of IBU, 120 g of DMP, 188 g of PPA, 114 g of lactose, 442 g of crystalline cellulose, 111 g of HPC-L and 110 g of L-HPC, and the charged was granulated with stirring by adding 884 g of pure water, and dried at 40° C. in vacuo for 14 hours. The dried product was comminuted by using a pulverizer (Power Mill, P-3S, manufactured by Showa Chemical Machinery Co., Ltd., Japan) provided with a punching screen of 1.5 mm φ to give 2,010 g of a comminuted powder (hereinbelow may be referred to as IDP).

On the other hand, a mixture of 1,500 g of CAF, 124 g of lactose, 464 g of crystalline cellulose, 116 g of HPC-L and 116 g of L-HPC was stirred and granulated while adding pure water using a high-rate stirring type granulator, and 2,105 g of CAF comminuted powder was obtained from the granulated product in the same procedures as in IDP comminuted powder.

A mixed powder was obtained by mixing 884 g of the IDP comminuted powder, 116 g of the CAF comminuted powder, 333 g of crystalline cellulose, 60 g of L-HPC and 7 g of magnesium stearate with a tumble mixer (Tumbler Mixer, TM-15, manufactured by Showa Chemical Machinery Co., Ltd., Japan) for one minute, and the resultant mixed powder was compression-molded with a rotary tablet machine (Correct 19K, manufactured by Kikusui Seisakusho Co., Ltd., Japan) with a punch of 9.5 mm φ to prepare about 4,300 tablets (weight: 280 mg per tablet, lenticular form or shape, about 5 mm in thickness).

Example 3

The high-shear type granulator was charged with 1,350 g of IBU, 144 g of DMP, 225 g of PPA, 225 g of CAF, 636 g of corn starch, 300 g of crystalline cellulose, 30 g of HPC-L and 90 g of ECG 505, and the charged was stirred and granulated by adding 600 g of pure water. The obtained product was extruded with an extrusion-granulator provided with a punching screen of 0.7 mm φ into cylindrical or columnar form, and rounded with Marumerizer into spherical granules. The spherical granules were dried in vacuo at 40° C. for 10 hours to give 2,840 g of spherical granules. A capsule was filled with the spherical granules by using a capsule filling machine (Zanasi 6F, manufactured by IMA Co., Ltd., Italy) to prepare a No. 1 capsule (total weight: 340 mg) having a long diameter of about 19 mm.

Comparative Example 1

The procedures of Example 2 were followed without using the CAF comminuted powder to give 4,200 lenticular tablets having a weight of 275 mg per tablet and a thickness of about 5 mm.

Experimental Example 1

A glass bottle was charged with the tablet obtained in Example 2 and Comparative Example 1 respectively and sealed. After storage at 60° C. for 2 weeks, the content of each active ingredient was determined using high performance liquid chromatography. The residual ratio relative to the initial content of the ingredient before storage was calculated according to the following formula, and the change of the external appearance was observed with the naked eye. The results are set forth in Table 1.

Residual ratio (%)=(content after storage at 60° C./content before storage)×100

TABLE 1

|  | Present Invention (Tablet of Example 2) | Control (Tablet of Com. Ex. 1) |
| --- | --- | --- |
| IBU | 98% | 88% |
| DMP | 97% | 83% |
| PPA | 92% | 77% |
| CAF | 100% | — |
| External appearance | no change | changed to yellow |

As apparent from the Table 1, in the pharmaceutical preparation of the present invention, even when the active ingredients were not grouped or incorporated separately, the contents of IBU, DMP and PPA, and the external appearance are stabilized by addition of CAF.

Experimental Example 2

A glass bottle was charged with the fine granule of Example 1 or the capsule of Example 3, and sealed. After being stored at 40° C, at 57% RH (relative humidity) for 4 weeks, the residual ratio of each ingredient was determined in the same manner as in Experimental Example 1, and results are shown in Table 2.

TABLE 2

|  | Example 1 | Example 3 |
| --- | --- | --- |
| IBU | 99% | 101% |
| DMP | 101% | 100% |
| PPA | 100% | 100% |
| CAF | 99% | 100% |

As clearly shown in Table 2, the pharmaceutical preparations of the present invention are stabilized and the content of each of the active ingredients is maintained at high level even when IBU, DMP, PPA and CAF are incorporated into the same group.

Example 4

To the high-shear type granulator were charged 1,350 g of IBU, 144 g of DMP, 225 g of PPA, 250 g of CAF, 1.5 g of alkaloids of belladonna extract, 241.5 g of corn starch, 420 g of crystalline cellulose, 84 g of HPC-L and 84 g of L-HPC, and the charged was granulated with stirring by adding 1,000 g of pure water. The product was extruded into fine cylindrical or columnar form by using an extrusion-granulator provided with a punching screen of 0.9 mm φ, and rounded with Marumerizer into spherical granules. The obtained spherical granules were dried at 40° C. in vacuo for 16 hours to give 2,650 g of granules.

Comparative Example 2

IBU (1,350 g), DMP (144 g), PPA (225 g), crystalline cellulose (450 g), HPC-L (90 g), L-HPC (90 g) and lactose (651 g) were charged into the high-shear type granulator, and the charged was stirred and granulated with adding 1,000 g of pure water. The granulated products were extruded into fine cylindrical or columnar form with an extrusion-granulator equipped with a punching screen of 0.7 mm φ, and rounded into spherical granules by using Marumerizer. The spherical granules were dried at 40° C. in vacuo for 16 hours to obtain 2,860 g of granules.

Examples 5 to 9

Granules were obtained in the same manner as in Comparative Example 2 except that a part of lactose was substituted with CAF to adjust the proportion of CAF to 1% by weight (Example 5), 2% by weight (Example 6), 3% by weight (Example 7), 4% by weight (Example 8) and 6% by weight (Example 9) based on the total weight of the granulated product.

Experimental Example 3

A glass bottle was charged with the granule obtained in Comparative Example 2, or Examples 5 to 9 respectively. After sealing the bottle, the bottle was stored at 60° C. for 2 weeks, and the content of each ingredient was determined by a high performance liquid chromatography and the residual ratio was calculated to give the results shown in Table 3.

TABLE 3

| CAF content in granule | Residual ratio of active ingredient | | | |
|---|---|---|---|---|
| | IBU | DMP | PPA | CAF |
| 0% | 90% | 84% | 82% | — |
| 1% | 94% | 89% | 83% | 100% |
| 2% | 96% | 92% | 91% | 100% |
| 3% | 96% | 95% | 93% | 100% |
| 4% | 98% | 96% | 95% | 100% |
| 6% | 99% | 97% | 96% | 100% |

What is claimed is:

1. A solid pharmaceutical preparation stabilized against decomposition which comprises effective amounts of a dextromethorphan, a phenylpropanolamine and ibuprofen as active ingredients, and a caffeine as a stabilizer, the content of the caffeine being 0.5 to 1,000 parts by weight relative to 100 parts by weight of each of said active ingredients.

2. A method of producing a solid pharmaceutical preparation, stabilized against decomposition, which comprises incorporating a stabilizing amount of a caffeine into a solid pharmaceutical preparation comprising a dextromethorphan, a phenylpropanolamine and ibuprofen as active ingredients, the amount of the caffeine being 0.5 to 1,000 parts by weight relative to 100 parts by weight of each of said active ingredients.

3. A stabilized solid pharmaceutical preparation according to claim 1, wherein ibuprofen is contained in a granule containing dextromethorphan.

4. A stabilized solid pharmaceutical preparation according to claim 1, in which (a) ibuprofen and the dextromethorphan, and (b) the phenylpropanolamine are respectively contained in different granules.

5. A stabilized solid pharmaceutical preparation according to claim 1, wherein the caffeine is contained in a proportion of 1 to 1,000 parts by weight relative to 100 parts by weight of the total weight of said active ingredients.

6. A stabilized solid pharmaceutical preparation according to claim 1, which comprises 1 to 15% by weight of the dextromethorphan, 1 to 20% by weight of the phenylpropanolamine, 5 to 70% by weight of ibuprofen and 1 to 80% by weight of the caffeine based on the total weight of the pharmaceutical preparation.

7. A stabilized solid pharmaceutical preparation according to claim 1, wherein 5 to 500 parts by weight of the caffeine is contained relative to 100 parts by weight of the total weight of said active ingredients.

8. A method according to claim 2, which comprises granulating the phenylpropanolamine, the dextromethorphan, ibuprofen and the caffeine with a carrier.

9. A method according to claim 2, wherein (a) granules containing the dextromethorphan, ibuprofen and the phenylpropanolamine, and (b) granules containing the caffeine are mixed.

10. A method according to claim 2, wherein the caffeine which may be granulated is present with a mixture of (a) granules containing the dextromethorphan and ibuprofen, and (b) granules containing the phenylpropanolamine.

11. A stabilized solid pharmaceutical preparation according to claim 1 composed of a granule containing the dextromethorphan, a granule containing the phenylpropanolamine and a granule containing ibuprofen.

12. A stabilized solid pharmaceutical preparation according to claim 1, which comprises (1) granules wherein the caffeine is combined with the dextromethorphan, the phenylpropanolamine and ibuprofen, or (2) a mixture of a granule containing the dextromethorphan, the phenylpropanolamine and ibuprofen and a granule containing the caffeine.

13. A stabilized solid pharmaceutical preparation according to claim 1, which comprises granules containing the dextromethorphan and ibuprofen, granules containing the phenylpropanolamine, and the caffeine, wherein the granules containing the phenylpropanolamine do not contain a reducing sugar or, contain the reducing sugar wherein the content of the reducing sugar is in a proportion of 10% by weight or less relative to the total weight of granules containing the phenylpropanolamine.

14. A stabilized solid pharmaceutical preparation according to claim 1, which is in the form of fine granules, granules, pills, tablets or filled capsules.

15. A stabilized solid pharmaceutical preparation according to claim 1, which is a pharmaceutical composition for a cold remedy.

16. A method according to claim 2, wherein 7 to 500 parts by weight of the caffeine is present relative to 100 parts by weight of the total weight of the said active ingredients.

* * * * *